United States Patent [19]

Overmyer

[11] Patent Number: 5,443,385
[45] Date of Patent: Aug. 22, 1995

US005443385A

[54] METHOD OF DISINFECTING AND LUBRICATING DENTAL/MEDICAL DEVICE

[76] Inventor: Thad J. Overmyer, 132 N. Second St., Danville, Ky. 40422

[21] Appl. No.: 237,872

[22] Filed: May 3, 1994

[51] Int. Cl.⁶ .......................... A61C 1/02; A61L 2/08; A61L 2/00
[52] U.S. Cl. ...................... 433/104; 422/27; 422/28
[58] Field of Search ..................... 433/104; 422/27, 28

[56] References Cited

U.S. PATENT DOCUMENTS 4,695,255  9/1987  Overmyer ........................... 433/215
5,318,443  6/1994  Overmyer ........................... 433/104

Primary Examiner—Nicholas D. Lucchesi
Attorney, Agent, or Firm—Charles J. Borwn

[57] ABSTRACT

A method of disinfecting and lubricating a discrete dental-medical device which comprises immersing the device in a water-alcohol-glycerin-chlorhexidine solution which includes methylcellulouse as a lubrication-enhancing and film-forming agent and polyglycol as an antifoaming agent, followed by autoclaving the device.

6 Claims, No Drawings

METHOD OF DISINFECTING AND LUBRICATING DENTAL/MEDICAL DEVICE

BACKGROUND OF THE INVENTION

Health care practitioners treating patients in succession commonly make repeated use of devices and tools which necessarily operate in contact with body fluid and/or tissue and which therefore require thorough disinfecting and sterilizing between each patient use. Such devices, referred to herein as dental-medical devices, often have moving parts, typically in their interior. These moving parts define interstices in which body fluid and tissue can lodge and present difficulties in removal. An example of such a device is a dental turbine handpiece.

Not only must such devices be disinfected and sterilized between uses but their moving parts require frequent lubrication for optimum operation. My U.S. application Ser. No. 08/079,410 filed Jun. 31, 1993, entitled "Method of Flushing, Disinfecting and Lubricating a Dental Turbine Handpiece", discloses a method of forcing a pressurized solution of disinfectant and lubricant simultaneously through a dental handpiece. The disclosed solution comprises water, glycerin and chlorhexidine gluconate. Dental debris is flushed from the device, including the moving parts within its interior, and after subsequent autoclaving a residuum of the solution is left as a lubricant for the moving parts.

Earlier in my U.S. Pat. No. 4,695,255 I disclosed a solution of about 25% to 70% (specifically 40%) by volume of water, about 5% to 35% (specifically 20%) by volume of potable alcohol such as ethanol and about 10% to 45% (specifically 40%) by volume of glycerin. That patent discloses the use of such a solution for cooling and lubricating human hard tissue during power tool cutting. The alcohol functions as a disinfectant and the glycerin serves as a lubricant.

It is the principal object of the present invention to improve upon the solutions described above to enhance lubricity and, in doing so, to prevent foaming.

SUMMARY OF THE INVENTION

The invention provides a method of disinfecting and lubricating a discrete dental-medical device. The term "discrete" as used herein means a device capable of being disconnected from other components and handled as a separate unit. The device is immersed in a solution which comprises about 35% to about 60% by volume of water, about 3% to about 20% by volume of potable alcohol, about 40% to about 50% by volume of glycerin, about 0.01% to about 2.0% by volume of chlorhexidine gluconate, about 0.01% to 5% by volume of polyglycol and about one gram of methylcellulouse per liter of solution. Thereafter the device is autoclaved by exposure to heated pressurized steam.

The device, such as a dental handpiece, may have interior moving parts, and the method may include the step of flushing of the device including its interior parts before the immersion step. The glycerine content is preferably about 50% by volume and the polyglycol content of the solution is preferably about 1% by volume. The alcohol may be ethanol. The device may be immersed in the solution for at least about ten minutes.

DESCRIPTION OF PREFERRED EMBODIMENT

It is appropriate to define the terms used herein for the components of the solution used in the method of the invention.

The water base is preferably distilled water and the potable alcohol is preferably ethanol. Glycerin means a commercial grade of the oily liquid obtained by the saponification of fats and fixed oils and containing glycerol in high concentration, usually with a small amount of water, and suitable for human consumption. A pharmaceutical form is sold by the Dow Chemical Company under the trademark OPTIUM.

Chlorhexidine gluconate is commercially available in liquid form, commonly designated simply chlorhexidine.

Polyglycol is a polymer of alkylene oxides, such as ethylene oxide, propylene oxide or butylene oxide. Polyglycols suitable for human consumption are available from the Dow Chemical Company for use as foam control agents in the form of polyproplyene glycols or polyglycol copolymers. Polypropylene glycol is preferred.

Methylcellulouse is a methyl ether of cellulouse typically containing from about 26% to about 33% of methoxy (OCHHH) group. It is available from the Dow Chemical Company in water-soluble powdered form suitable for human consumption under the trademarks METHOCEL and ETHOCEL. It has been found that METHOCEL is particularly suitable for the practice of this invention. The methylcellulouse component of the solution used in the method of the invention serves to increase the lubricity of the glycerin and contribute to film formation. The viscosity of the solution varies directly with the amount of methylcellulouse present and is therefore an indicator of lubricity. The presence of methylcellulouse results, however, in a tendency to foaming in the solution and therefore the polyglycol is added because it is known as an antifoaming agent.

Various tests were carried out under laboratory conditions to determine the appropriate amount of methylcellulouse and polyglycol to be added to various water-alcohol-glycerin-chlorhexidine gluconate solutions. Lubricity is a function of viscosity but excessive viscosity hinders the operation of the moving parts of the device and can clog the device so that it becomes inoperable. It was apparent from the tests that viscosity became greater as a result of the final step of autoclaving under steam at high pressure and high temperature.

In one test 400 ml. of distilled water, 500 ml. of glycerin, 89 ml. of ethanol and 1 ml. of chlorhexidine gluconate were mixed and 1 gram of methylcellulouse in powdered form was added. To inhibit foaming 10 ml. of polypropylene glycol were also added. A dental turbine handpiece was the device used in the test and it was immersed in the solution for approximately ten minutes. Autoclaving was carried out under steam pressure and temperature and duration within manufacturing guidelines. Standard viscosity tests showed that improved lubricity resulted without clogging, both before and after autoclaving.

In a second test the amount of methycellulouse was doubled to 2 grams while the other components remained the same. This increased the viscosity of the solution to the point where the dental handpiece was clogged and could not operate after immersion, even before autoclaving. A third test, differing from the second only in that the amount of methylcellulouse was reduced to 1.5 grams, still demonstrated excess viscosity.

In a fourth test the components and their amounts in the first test were repeated except that the water content was increased to 500 ml. and the glycerin was reduced to 400 ml. Lubricity was satisfactory though not quite to the degree of the more glycerin-rich solution of the first test, and again viscosity did not adversely affect the operation of the handpiece.

Since foaming results from addition of methylcellulouse, polyglycol in the form of polypropylene glycol was present in each test in about 1% by volume of the solution. Polyglycol is also known for its ability to prevent metal corrosion.

From operation of dental handpieces subjected to flushing and immersion in those solutions which the tests indicated to be satisfactory, it is concluded that good results are obtainable with a solution comprising about 35% to about 60% by volume of distilled water, about 3% to about 20% by volume of ethanol, about 50% by volume of glycerin, about 0.01% to about 2.0% by volume of chlorhexidine gluconate, about 1% by volume of polypropylene glycol, and about one gram of methylcellulouse per liter of solution. It is reasonable to extend these parameters somewhat so that broadly the solution can comprise about 35% to about 60% by volume of water, about 3% to about 20% by volume of potable alcohol, about 40% to about 50% by volume of glycerin, about 0.01% to about 2.0% by volume of chlorhexidine gluconate, about 0.01% to about 5.0% by volume of polyglycol and about one gram of methylcellulouse per liter of solution.

The scope of the method of the invention is to be determined from the following claims rather than the foregoing description of a preferred embodiment.

I claim:

1. A method of disinfecting and lubricating a discrete dental-medical device which comprises
   a) immersing said device in a solution comprising
      i. about 35% to about 60% by volume of water,
      ii. about 3% to about 20% by volume of potable alcohol,
      iii. about 40% to about 50% by volume of glycerin,
      iv. about 0.01% to about 2.0% by volume of chlorhexidine gluconate,
      v. about 0.01% to about 5.0% by volume of polyglycol; and
      vi. about one gram of methylcellulouse per liter of solution, and
   b) autoclaving the device by exposure to heated pressurized steam.

2. A method according to claim 1 wherein said device has interior moving parts and which includes the step of flushing said device including its interior parts.

3. A method according to claim 1 wherein the glycerin content of the solution is about 50% by volume.

4. A method according to claim 1 wherein the polyglycol content is polypropylene glycol and its content in the solution is about 1% by volume.

5. A method according to claim 1 wherein said device is immersed in said solution for at least about ten minutes.

6. A method of disinfecting and lubricating between use on patients a dental handpiece having interior moving parts which comprises
   a) immersing said device for at least about ten minutes in a solution comprising
      i. about 35% to about 60% by volume of distilled water,
      ii. about 3% to about 20% by volume of potable ethanol;
      iii. about 50% by volume of glycerin,
      iv. about 0.01% to about 2.0% by volume of chlorhexidine,
      v. about 1% by volume of polypropylene glycol; and
      vi. about one gram of methylcellulouse per liter of solution;
   b) flushing said device including its interior parts; and
   c) autoclaving the device by exposure to heated pressurized steam.

* * * * *